US012782267B2

(12) United States Patent
Petrov et al.

(10) Patent No.: US 12,782,267 B2
(45) Date of Patent: Nov. 3, 2026

(54) DETECTION APPARATUS WITH OPTICAL DETECTOR AND PARTICLE DETECTION METHOD

(71) Applicant: Artilux, Inc., Menlo Park, CA (US)

(72) Inventors: Konstantin P. Petrov, Hsinchu County (TW); Neil Y. Na, San Jose, CA (US)

(73) Assignee: Artilux, Inc., Menlo Park, CA (US)

( * ) Notice: Subject to any disclaimer, the term of this patent is extended or adjusted under 35 U.S.C. 154(b) by 121 days.

(21) Appl. No.: 19/055,277

(22) Filed: Feb. 17, 2025

(65) Prior Publication Data

US 2025/0277736 A1 Sep. 4, 2025

Related U.S. Application Data

(60) Provisional application No. 63/652,065, filed on May 27, 2024, provisional application No. 63/560,777, filed on Mar. 4, 2024.

(51) Int. Cl.

*G01N 21/17* (2006.01)
*G01N 21/3504* (2014.01)
*G01N 33/98* (2006.01)

(52) U.S. Cl.

CPC ......... *G01N 21/17* (2013.01); *G01N 21/3504* (2013.01); *G01N 33/98* (2013.01); *G01N 2021/1785* (2013.01); *G01N 2021/1795* (2013.01); *G01N 2201/0221* (2013.01)

(58) Field of Classification Search

CPC .... G01N 21/17; G01N 21/3504; G01N 33/98; G01N 2021/1785; G01N 2021/1795; G01N 2201/0221; G01N 21/359; G01N 2015/1445; G01N 15/1434; G01N 15/075; G01N 15/1433

See application file for complete search history.

(56) References Cited

U.S. PATENT DOCUMENTS

| | | | | |
|---|---|---|---|---|
| 8,193,502 | B2 | 6/2012 | Hodgkinson et al. | |
| 11,181,472 | B2 | 11/2021 | Stock et al. | |
| 11,467,088 | B2 | 10/2022 | Kim et al. | |
| 11,625,002 | B2 * | 4/2023 | Hong ................. | G01N 15/0227 348/40 |

(Continued)

FOREIGN PATENT DOCUMENTS

| | | |
|---|---|---|
| CN | 109781639 | 5/2019 |
| WO | WO2024116593 | 6/2024 |

*Primary Examiner* — Seung C Sohn

(74) *Attorney, Agent, or Firm* — Dority & Manning, P.A.

(57) ABSTRACT

An example method for detecting target particles in a detection apparatus includes receiving, by at least one processor of the detection apparatus, a first image data at a first wavelength from an image sensor of the detection apparatus. The method includes receiving, by the at least one processor, a second image data at a second wavelength from a particle detector of the detection apparatus. The method includes obtaining, by the at least one processor, a 2D image based on the first image data. The method includes obtaining, by the at least one processor, a depth map data based on the first image data. The method includes obtaining, by the at least one processor, a particle map data based on a ratio of the second image data to the 2D image. The method includes determining, by the at least one processor, a concentration result based on the depth map data and the particle map data.

20 Claims, 7 Drawing Sheets

(56) References Cited

U.S. PATENT DOCUMENTS

| | | | |
|---|---|---|---|
| 2011/0314901 | A1 | 12/2011 | Lee |
| 2013/0145813 | A1 | 6/2013 | Pleban |
| 2016/0231244 | A1 | 8/2016 | Camargo et al. |
| 2017/0003222 | A1 * | 1/2017 | Neijzen .............. G01N 15/1436 |
| 2021/0396658 | A1 | 12/2021 | Denda et al. |

* cited by examiner

DETECTION APPARATUS WITH OPTICAL DETECTOR AND PARTICLE DETECTION METHOD

RELATED APPLICATIONS

The subject application claims the benefit of priority to U.S. Provisional Patent Application No. 63/560,777 filed on Mar. 4, 2024, entitled "A Detection Apparatus with Optical Detector," and U.S. Provisional Patent Application No. 63/652,065 filed on May 27, 2024, entitled "A Detection Apparatus with Optical Detector," both of which are incorporated by reference herein in their entirety for all purposes.

FIELD

The present disclosure relates generally to a detection apparatus with an optical sensor device and a method used to detect the presence of target particles or the concentration of the target particles in a reference substance, for example, the alcohol concentration in the breathing air.

BACKGROUND

Optical sensor devices are being used in many systems, such as smartphones, wearable electronics, robotics, and autonomous vehicles, etc. for proximity detection, 2D/3D imaging, object recognition, image enhancement, material recognition, color fusion, health monitoring, and other relevant applications. The optical sensor device can be operable for different wavelength ranges, including visible (e.g., wavelength range 380 nm to 780 nm, or a similar wavelength range as defined by a particular application) and non-visible light. The non-visible light includes near-infrared (NIR, e.g., wavelength range from 780 nm to 1000 nm, or a similar wavelength range as defined by a particular application) and short-wavelength infrared (SWIR, e.g., wavelength range from 1000 nm to 3000 nm, or a similar wavelength range as defined by a particular application) light.

SUMMARY

Aspects and advantages of embodiments of the present disclosure will be set forth in part in the following description, or may be learned from the description, or may be learned through practice of the embodiments.

One example aspect of the present disclosure is directed to a method for detecting target particles in a detection apparatus. The method includes receiving, by at least one processor of the detection apparatus, a first image data at a first wavelength from an image sensor of the detection apparatus. The method includes receiving, by the at least one processor of the detection apparatus, a second image data at a second wavelength from a particle detector of the detection apparatus. The method includes obtaining, by the at least one processor of the detection apparatus, a 2D image based on the first image data. The method includes obtaining, by the at least one processor of the detection apparatus, depth map data based on the first image data. The method includes obtaining, by the at least one processor of the detection apparatus, a particle map data based on a ratio of the second image data to the 2D image. The method includes determining, by the at least one processor of the detection apparatus, a concentration result based on the depth map data and the particle map data.

In some implementations, the method includes determining, by the at least one processor of the detection apparatus, a 3D image based on the first image data.

In some implementations, the method includes storing, by the at least one processor of the detection apparatus, a calibration parameter obtained from a ratio of light output power of the image sensor and the particle detector.

In some implementations, the method includes determining, by the at least one processor of the detection apparatus, a concentration result based on the calibration parameter, the depth map data, and the particle map data.

In some implementations, the image sensor includes a plurality of photodetectors forming a pixel array and at least one light emitter.

In some implementations, at least a portion of the pixel array is a time-of-flight sensor.

In some implementations, the particle detector includes a light emitter and an optical detector.

In some implementations, the optical detector includes germanium (Ge), tin (Sn), and silicon (Si).

In some implementations, the first wavelength is different from the second wavelength.

In some implementations, light with the first wavelength is not absorbed by the target particles.

In some implementations, the at least one processor includes a 3D image calculating module configured to provide a 3D image, a particle map calculating module configured to provide the particle map data, and a concentration calculating module configured to provide the concentration result.

In some implementations, the particle map data contains the particle distribution information.

In some implementations, the concentration result is an average concentration of the target particles.

In some implementations, the concentration result is a total amount of the target particles.

Another example aspect of the present disclosure is directed to a detection apparatus configured to detect target particles. The detection apparatus includes an image sensor configured to provide a first image data at a first wavelength, a particle detector configured to provide the second image data at a second wavelength, and at least one processor coupling to the image sensor and the particle detector. The at least one processor is configured to: receive the first image data; receive the second image data; obtain a 2D image based on the first image data; obtain depth map data based on the first image data; obtain a particle map data based on a ratio of the second image data to the 2D image; and determine a concentration result based on the depth map data and the particle map data.

In some implementations, the at least one processor is configured to determine a 3D image based on the first image data.

In some implementations, the at least one processor is configured to store a calibration parameter obtained from a ratio of light output power of the image sensor and the particle detector.

In some implementations, the at least one processor is configured to determine a concentration result based on the calibration parameter, the depth map data, and the particle map data.

In some implementations, the image sensor includes a plurality of photodetectors forming a pixel array and at least one light emitter.

In some implementations, at least a portion of the pixel array is a time-of-flight sensor.

BRIEF DESCRIPTION OF THE DRAWINGS

The foregoing aspects and many of the advantages of this application will become more readily appreciated as the same becomes better understood by reference to the following detailed description, when taken in conjunction with the accompanying drawings.

DETAILED DESCRIPTION

Figure 1:
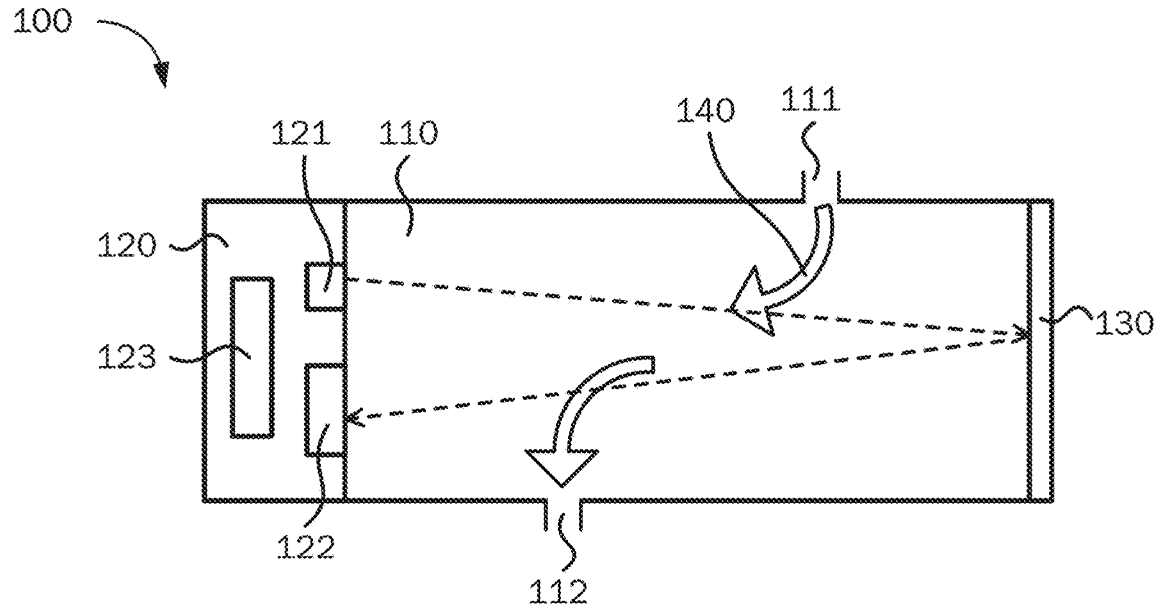
FIG. 1 shows a view of a detection apparatus in accordance with one embodiment of the present disclosure.

The following embodiments accompany the drawings to illustrate the concept of the present disclosure. In the drawings or descriptions, similar or identical parts use the same reference numerals, and in the drawings, the shape, thickness, or height of the element can be reasonably expanded or reduced. The embodiments listed in the present application are only used to illustrate the present application and are not used to limit the scope of the present application. Any obvious modification or change made to the present application does not depart from the spirit and scope of the present application.

The present disclosure relates to a detection apparatus that can include an optical sensor device to detect the presence of the target particles and/or the concentration of the target particles in the reference substance. For example, an alcohol detection apparatus can be used to detect the concentration of ethanol in the liquid or gas. The liquid can be water, blood, etc. The gas can be air, e.g., breathing air exhaled by a person. The detection apparatus can be installed in a portable device used by a person, for example, to perform alcohol detection before driving vehicles or entering a certain area. The portable device may be a mobile phone, a handheld instrument, an earbud, a pair of glasses, a helmet, a wristband, a watch, a ring, etc.

FIG. 1 shows a view of a detection apparatus in accordance with one embodiment of the present disclosure. The detection apparatus 100 includes a chamber 110, an optical sensor device 120, and a reflector 130. The detection apparatus 100 also includes an inlet 111 and an outlet 112, allowing the reference substance 140 to enter the chamber 110 from the inlet 111 and exit the chamber 110 through the outlet 112 for detection. The optical sensor device 120 is located at one end of the chamber 110. The reflector 130 is located at another end of the chamber 110 and faces the optical sensor device 120. The reflector 130 can be made of metal, insulating material, or a combination thereof and configured to reflect light from the optical sensor device 120. When the reference substance 140 passes through the chamber 110, the optical sensor device 120 can detect the presence and/or the concentration of the target particles in the reference substance 140 by optical measurement. For example, the inlet 111 is a mouthpiece through which a person can blow breathing air as a reference substance 140 into the chamber 110. The reference substance 140, that is, the gas of the breathing air, enters the chamber 110 through the inlet 111 and exits the chamber 110 through the outlet 112. The optical sensor device 120 is capable of detecting the presence and/or concentration of alcohol in the breathing air. For another example, an alcohol-containing liquid enters the chamber 110 from the inlet 111 and exits the chamber 110 through the outlet 112. The optical sensor device 120 is capable of detecting the presence and/or concentration of alcohol in the liquid.

As shown in FIG. 1, the optical sensor device 120 includes a light emitter 121, an optical detector 122, and at least one processor 123. The processor 123 couples to the light emitter 121 and is configured to control the light emitter 121 (e.g., turn on/off, the power level, emission period, spectrum, frequency of emission, etc.). The processor 123 also couples to the optical detector 122 and is configured to calculate and determine the presence and/or concentration of the target particles in the reference substance 140 based on the received light intensity from the optical detector 122. The processor 123 can be implemented in numerous ways, with software and/or hardware (e.g., digital signal processor (DSP), general purpose processor, application-specific integrated circuit (ASIC), analog circuitry, digital circuitry, any combinations thereof, etc.), to perform the various functions. When the reference substance 140 (e.g., liquid or gas) with the target particles passes through the chamber 110, the light emitter 121 emits a testing optical signal passing through the reference substance 140 and then reaching the reflector 130. A portion of the testing optical signal is reflected by the reflector 130 and received by the optical detector 122. The wavelength of the testing optical signal emitted from the light emitter 121 can be selected from a plurality of wavelengths with high absorbance or low transmittance relative to the target particles. When the testing optical signal emitted from the light emitter 121 passes through the reference substance 140, a portion of the testing optical signal is absorbed by the target particles, while the other portion of the testing optical signal passes through the reference substance 140 and is reflected to the optical detector 122. Since a portion of the testing optical signal is absorbed by the target particles, the light intensity detected by the optical detector 122 should be less than the intensity of the testing optical signal emitted from the light emitter 121. The processor 123 can compare the intensity difference between the testing optical signal from the light emitter 121 and the light received by the optical detector 122 to determine the presence and/or concentration of the target particles in the reference substance 140 through mathematical calculations.

The optical detector 122 can include a single photoelectronic device or a plurality of photoelectronic devices arranged in an array. In an embodiment, the optical detector 122 includes a plurality of photoelectronic devices arranged in a one-dimensional array or a two-dimensional array. The photoelectronic device can include a supporting substrate and a detecting region supported by the supporting substrate.

The detecting region can include group IV materials or group III-V materials and is configured to absorb photons. The group IV materials can include silicon (Si) or germanium (Ge). The group III-V materials can include Al, Ga, In, N, P, As, Sb, or any combination thereof. The supporting substrate can include a material, such as silicon, different from that of the detecting region. The optical detector 122 can detect visible light, or non-visible light according to the application. The visible light can include blue, navy, green, yellow, or red light. The non-visible light can include NIR or SWIR.

The light emitter 121 can be semiconductor light-emitting elements, such as a light-emitting diode (LED), a laser diode, a vertical-cavity surface-emitting laser (VCSEL), or an organic light-emitting diode (OLED). The light emitter 121 can emit light with a wavelength corresponding to the detecting wavelength of the optical detector 122.

Figure 2:
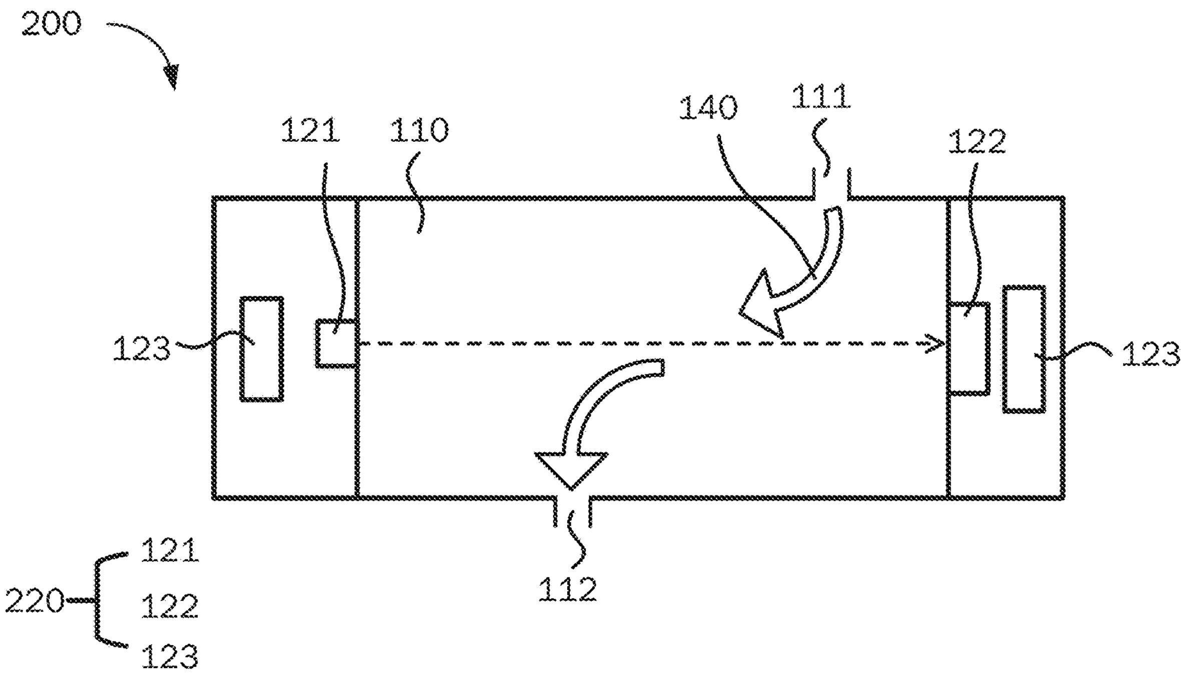
FIG. 2 shows a view of a detection apparatus in accordance with another embodiment of the present disclosure.

FIG. 2 shows a view of a detection apparatus in accordance with another embodiment of the present disclosure. The detection apparatus 200 includes a chamber 110 and an optical sensor device 220. The optical sensor device 220 includes a light emitter 121, an optical detector 122, and at least one processor 123. The detection apparatus 200 also includes an inlet 111 and an outlet 112, allowing the reference substance 140 to enter the chamber 110 from the inlet 111 and exit the chamber 110 through the outlet 112 for detection. The light emitter 121 is located at one end of the chamber 110 to emit the testing optical signal passing through the reference substance 140 and toward the optical detector 122. The optical detector 122 is located at another end of the chamber 110 and faces the light emitter 121 to receive the testing optical signal emitted from the light emitter 121. The at least one processor 123 couples to the light emitter 121 and is configured to control the light emitter 121 (e.g., turn on/off, the power level, emission period, spectrum, frequency of emission, etc.). The at least one processor 123 also couples to the optical detector 122 and is configured to calculate and determine the presence and/or concentration of the target particles in the reference substance 140 based on the received light intensity from the optical detector 122. The at least one processor 123 can be implemented in numerous ways, with software and/or hardware (e.g., digital signal processor (DSP), general purpose processor, application-specific integrated circuit (ASIC), analog circuitry, digital circuitry, any combinations thereof, etc.), to perform the various functions. When the reference substance 140 (e.g., liquid or gas) with the target particles passes through the chamber 110, the light emitter 121 emits a testing optical signal passing through the reference substance 140 and then reaching the optical detector 122. The wavelength of the testing optical signal emitted from the light emitter 121 can be selected from a plurality of wavelengths with high absorbance or low transmittance relative to the target particles. When the testing optical signal emitted from the light emitter 121 passes through the reference substance 140 and the target particles, a portion of the testing optical signal is absorbed by the target particles, while the other portion of the testing optical signal passes through the reference substance 140 and reaches the optical detector 122. Since a portion of the testing optical signal is absorbed by the target particles, the light intensity detected by the optical detector 122 should be weaker than the intensity of the testing optical signal emitted from the light emitter 121. The at least one processor 123 can compare the intensity difference between the testing optical signal from the light emitter 121 and the light received by the optical detector 122 to determine the presence and/or concentration of the target particles in the reference substance 140 through mathematical calculations.

The reference substance to be tested may be a mixture, which contains target particles mixed in the reference substance, such as alcohol mixed in the water, or alcohol mixed in the air. The target particles may have high absorbance or low transmittance relative to an optical signal with a specific wavelength. However, other substances that do not need to be detected (such as reference substance) also may have high absorbance or low transmittance relative to the optical signal with this specific wavelength. Therefore, the light intensity of the optical signal with this specific wavelength received by the optical detector is not only affected by the absorbance of the target particles but also by the absorbance of other substances that do not need to be detected, and the optical sensor device may obtain erroneous determination. In addition, the optical characteristics of the light emitter may change as the ambient temperature or usage time. The wavelength of the optical signal generated by the light emitter driven by the same driving current may change due to different ambient temperatures or long usage time. It would cause the wavelength of the optical signal to drift to a band easily interfered with by other substances that do not need to be detected.

Accordingly, before detecting the presence of target particles, the optical sensor device needs to determine a testing optical signal emitted from the light emitter and to be at a target wavelength. The target particles have high absorbance or low transmittance relative to the testing optical signal with the target wavelength, and other substances that do not need to be detected (such as reference substance) have low absorbance or high transmittance (for example, the light transmittance is greater than 98%) relative to the testing optical signal with the target wavelength. The process of determining the testing optical signal can reduce the influence of other substances on the detection of the presence or concentration of target particles, thereby improving the accuracy of detection results. Different wavelengths of the optical signal can be changed by applying various driving currents to the light emitter through the processor. Taking a gas sample as a reference substance as an example, the detection apparatus can be used to detect the presence or concentration of alcohol in the gas sample. In one case, the gas sample is breathing air containing a lot of moisture, so the optical sensor device needs to choose a testing optical signal with a target wavelength that is high absorbance or low transmittance relative to ethanol but low absorbance or high transmittance relative to water. When detecting the gas sample with alcohol, most of the testing optical signal is absorbed only by the alcohol and not by the water.

Figure 3:
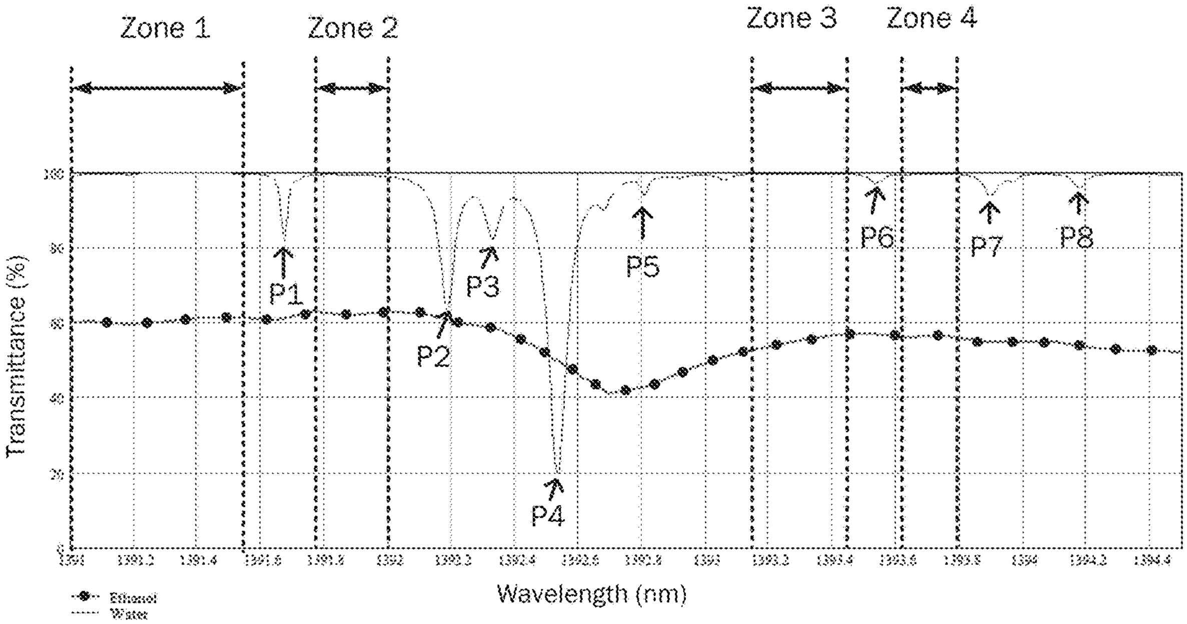
FIG. 3 shows the transmittance spectrums of water and ethanol.

FIG. 3 shows the transmittance spectrums of water and ethanol. FIG. 3 shows that alcohol has low transmittance (for example, the transmittance is less than 65%) relative to the multiple reference optical signals in the SWIR wavelength range of 1391 nm to 1394.4 nm. Therefore, the testing optical signals used to detect the presence and/or concentration of alcohol in the breathing air can choose from multiple reference optical signals in this SWIR wavelength range. As shown in FIG. 3, water also has low transmittance at multiple wavelengths of the reference optical signals, such as P1~P8. In other words, the light with one of the wavelengths P1~P8 can be absorbed by alcohol and also be absorbed by water. To ensure accurate detection results unaffected by moisture in the breathing air, the testing optical signal used to detect alcohol in the breathing air should not use wavelengths P1~P8. In one embodiment, it is preferable to choose a light with a wavelength within zone 1~zone 4 of reference optical signals shown in FIG. 3 as the testing optical light to detect the alcohol in the breathing air. Most of the testing optical signal with the wavelength within zone 1~zone 4 is absorbed by alcohol and not by water. Relative to the testing optical light at the wavelength within zone 1~zone 4, ethanol has high absorbance or low transmittance, while water has low absorbance or high transmittance (for example, the light transmittance is greater than 98%).

Figure 4:
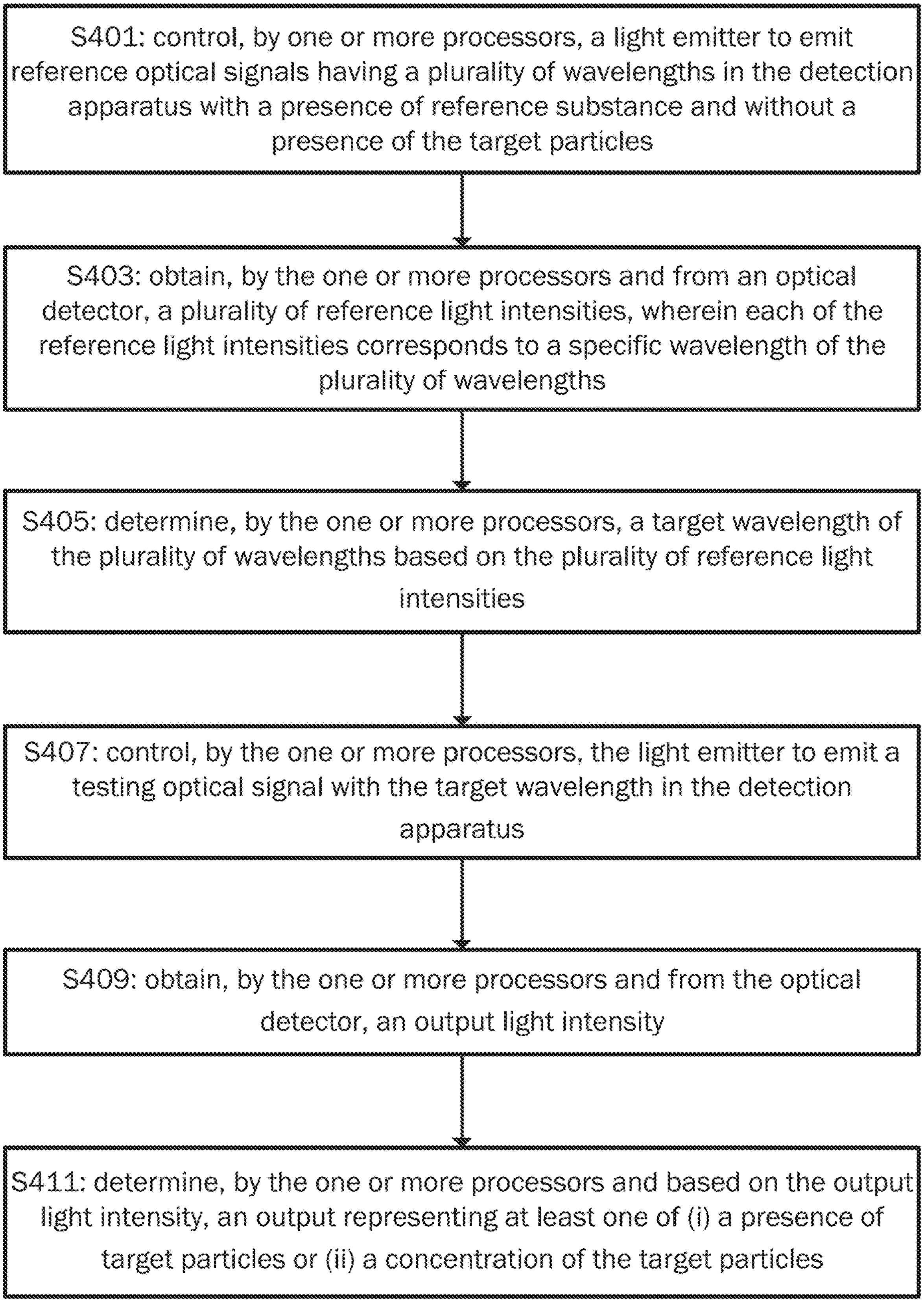
FIG. 4 shows a flowchart for detecting target particles of a detection apparatus in accordance with one embodiment of the present disclosure.

FIG. 4 shows a flow for detecting target particles of a detection apparatus in accordance with one embodiment of the present disclosure. In S401, one or more processors can control the light emitter to emit a plurality of reference optical signals having a plurality of wavelengths in the detection apparatus with the presence of reference substance and without the presence of the target particles. In an embodiment, the one or more processors can apply various driving currents to the light emitter to emit the plurality of reference optical signals having the plurality of wavelengths. The target particles have high absorbance or low transmittance relative to the plurality of reference optical signals. In another embodiment, the optical sensor device can include an adjustable filter disposed on the light path of the light emitter and one or more processors can control the adjustable filter to change the wavelength of the optical signal.

In S403, the one or more processors obtain a plurality of reference light intensities from the optical detector. Each of the reference light intensities corresponds to a specific wavelength of the plurality of wavelengths. The one or more processors also can record each of the driving currents corresponding to each of the reference light intensities. Since there is no presence of the target particles in the detection apparatus, the optical sensor device can recognize a portion of reference optical signals that can be absorbed by the reference substance that does not need to be tested by comparing each of the reference light intensities.

In S405, the one or more processors determine a target wavelength of the plurality of wavelengths based on the plurality of reference light intensities. The light intensity at the target wavelength would be strong due to the reference substance having low absorbance or high transmittance relative to the target wavelength. The one or more processors also can determine a target driving current corresponding to the target wavelength. In one implementation, the one or more processors can calculate a plurality of decision indices corresponding to each of the reference light intensities and determine the target wavelength based on the decision indices. The decision indices correlate to the absorbance and transmittance of the reference substance for the plurality of wavelengths. In another implementation, the optical sensor device can obtain a plurality of decision indices by comparing the intensity of each of the reference optical signals from the light emitter with the corresponding reference light intensity from the optical detector. In another implementation, the one or more processors determine the highest reference light intensity of the plurality of reference light intensities, and the one or more processors determine a target wavelength corresponding to a wavelength with the highest reference light intensity.

In S407, the one or more processors control the light emitter to emit a testing optical signal with the target wavelength in the detection apparatus. In an embodiment, a person can blow the breathing air into the detection apparatus through the inlet, and then one or more processors control the light emitter to emit a testing optical signal with the target wavelength in the detection apparatus for detecting the presence and/or concentration of alcohol in the breathing air. In another embodiment, a liquid is injected into the detection apparatus through the inlet, and then one or more processors control the light emitter to emit a testing optical signal with the target wavelength in the detection apparatus for detecting the presence or concentration of alcohol in the liquid. The target particles (e.g., ethanol) have high absorbance or low transmittance relative to the testing optical signal and the reference substance (e.g., water) has low absorbance or high transmittance relative to the testing optical signal. For example, the target wavelength of the testing optical signal can be within one of zone 1 to zone 4 in FIG. 3. The one or more processors can apply the target driving current corresponding to the target wavelength to drive the light emitter to generate the testing optical signal.

In S409, the one or more processors obtain an output light intensity from the optical detector. A small portion of the testing optical signal at the target wavelength may be absorbed by the reference substance. In an implementation, the one or more processors can calibrate the output light intensity based on the transmittance of the reference substance at the target wavelength to obtain more accurate light intensity affected by the target particles. In S411, the one or more processors determine an output representing at least one of (i) a presence of target particles or (ii) a concentration of the target particles based on the output light intensity. Since most of the testing optical signal is not absorbed by the reference substance, the output light intensity from the optical detector is only affected by the target particles, which can be used to determine the presence or concentration of the target particles through mathematical methods. In another implementation, the one or more processors determine the presence of the target particles by comparing whether the output light intensity is below a predetermined threshold. In another implementation, the one or more processors can display the output through a display component of the detection apparatus.

In an implementation, the light emitter 121 can be a tunable single-wavelength laser diode or VCSEL, which can precisely control the wavelength of the emitting light by controlling the driving current.

In an implementation, the mathematical methods used to determine the concentration of the target particles may be based on the Beer-Lambert law principle, which utilizes the absorption ratio of light to determine the concentration level of the target particles.

In another embodiment, the detection apparatus may be used to detect the target particles generated by a remote object and therefore does not have a chamber structure. For example, an alcohol detection apparatus is installed in a car to detect whether the driver's breath contains alcohol for safety. In the past, courts in some countries have required some drivers to use automatic car ignition interlock devices based on their criminal records, which are integrated and coupled to breathalyzers. However, some countries have now legislated to require new cars to install such automatic ignition devices to detect whether the driver's breath contains alcohol and perform driver identification to enhance public safety.

Figure 5:
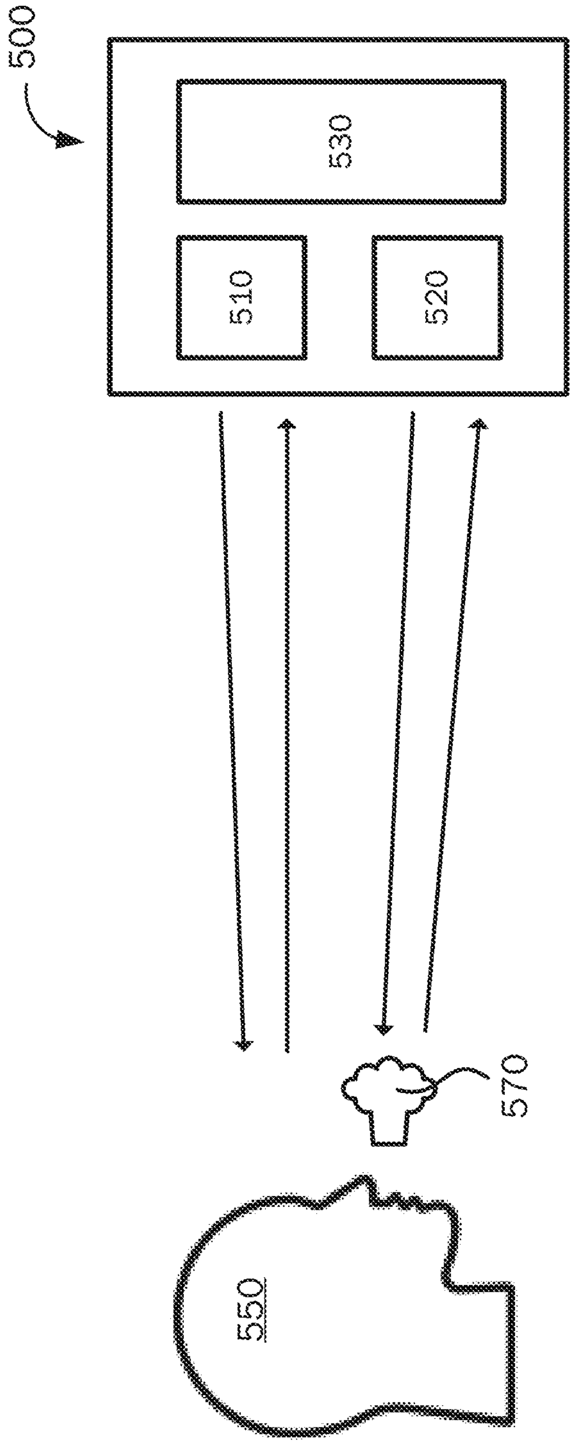
FIG. 5 shows a detection schematic diagram of a detection apparatus in accordance with another embodiment of the present disclosure.

FIG. 5 shows a detection schematic diagram of a detection apparatus in accordance with another embodiment of the present disclosure. For example, the detection apparatus 500 may be an alcohol detection apparatus and is disposed of in front of the driver's seat, facing the driver 550, to measure the ethanol concentration in the driver's breath 570 while performing facial recognition on the driver 550. The detection apparatus 500 utilizes a non-contact method and the detection results can be used to control the automatic car ignition interlock device. The detection apparatus 500 includes an image sensor 510, a particle detector 520, and at least one processor 530. The image sensor 510 is configured to provide 2D images and depth images for object recognition (e.g., facial recognition). The particle detector 520 may be implemented as an optical sensor device to provide optical image signals related to particle distribution (e.g., alcohol distribution). The processor 530 is configured to receive the signals from the image sensor 510 and the particle detector 520 to output the 3D image for object recognition and the particle concentration result.

Figure 6:
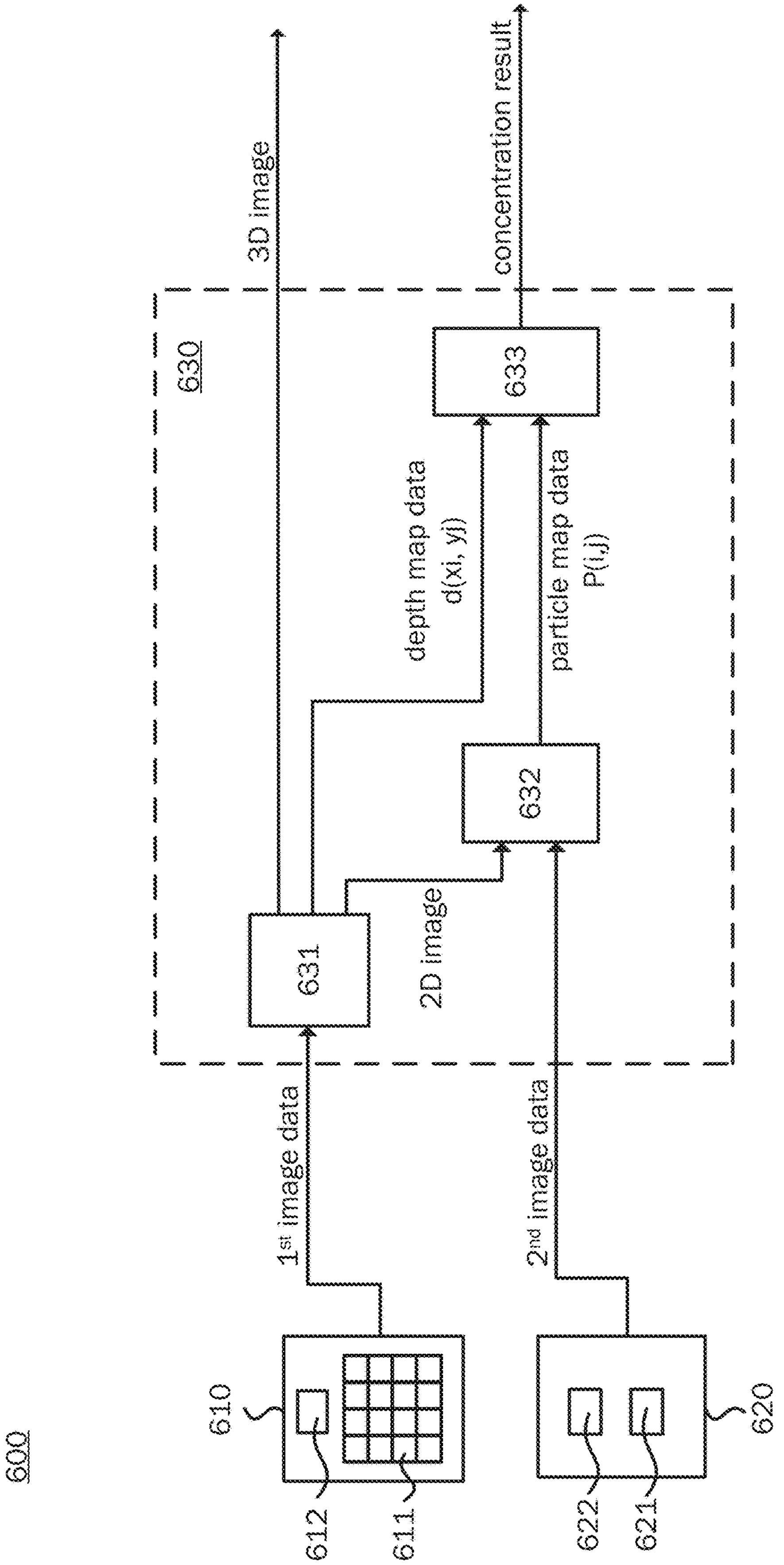
FIG. 6 shows a view of a detection apparatus in accordance with one embodiment of the present disclosure.

FIG. 6 shows a view of a detection apparatus in accordance with one embodiment of the present disclosure. The detection apparatus 600 is configured to output the 3D image for object recognition and the particle concentration result. The detection apparatus 600 may be the aforementioned detection apparatus 500, which operates in the vehicle to detect the driver's status. The detection apparatus 600 may include an image sensor 610, a particle detector 620, and at least one processor 630. The image sensor 610 is configured to provide $1^{st}$ image data for object recognition and may include a plurality of photodetectors to forming a pixel array 611 and at least one light emitter 612. The light emitter 612 may include a pulsed (e.g., the pulse width is around 3~10 ns) and high-power light source (e.g., around 1~3 W), such as a broad-stripe Fabry-Perot (FP) laser or a VCSEL array, operating at near-infrared (NIR) wavelengths. The $1^{st}$ image data may include depth map data and 2D image which is a non-depth image for object recognition (e.g., facial recognition). The 2D image includes the object morphology (e.g., facial morphology). The depth map data includes the distance information of each pixel from the detection apparatus 600 to the object (e.g., driver's face). At least a portion of the pixel array 611 may be one or more time-of-flight (ToF) sensors to provide the depth map data, that can be implemented by Ge-on-Si technology and operating at near-infrared (NIR) wavelengths.

The particle detector 620 can be implemented as an optical sensor device and can refer to the aforementioned optical sensor device 120. The particle detector 620 is configured to provide a $2^{nd}$ image data and may include an optical detector 621 and a light emitter 622. The light emitter 622 may include a steady-state, low-power light source (e.g., around 1 mW), which can be one of the light emitters shown in FIGS. 1~3. The light emitter 622 can emit light with a specific wavelength toward the remote object (e.g., driver), the specific wavelength of which can be absorbed by the target particle (e.g., ethanol) but not by the reference substance (e.g., water). The optical detector 621 may receive the light with the specific wavelength reflected from the remote object (e.g., driver) and generate the $2^{nd}$ image data which includes the object morphology and also can show the measurement of optical absorption by the target particle. The operating wavelength of the image sensor 610 is different from the operating wavelength of the particle detector 620. The image sensor 610 operates at a wavelength that is not absorbed by the target particle and is only used to provide image information of the remote object. For example, the image sensor 610 can operate at a wavelength close to 940 nm for 3D image sensing. The wavelength at which the particle detector 620 operates can be the CH-stretch overtone near 1750 nm or the OH-stretch overtone near 1393 nm. In an implementation, the optical detector 621 may include germanium (Ge) and silicon (Si) to detect light with a wavelength of 1393 nm. In another implementation, the optical detector 621 may include germanium (Ge), tin (Sn), and silicon (Si) to detect light with a wavelength of 1710 nm. Light close to the wavelength of 1393 nm will be absorbed by the water vapor that is always present in the air and interfere with the alcohol detection. Therefore, when detecting alcohol, the light emitter operating at 1393 nm is better to be a narrow-band and tunable laser.

The processor 630 may include a 3D image calculating module 631, a particle map calculating module 632, and a concentration calculating module 633. The 3D image calculating module 631 couples to the image sensor 610 to receive $1^{st}$ image data from the image sensor 610. The $1^{st}$ image data may include depth map data and 2D image which is a non-depth image. The 3D image calculating module 631 is configured to perform 3D image calculation and generate 3D image according to the $1^{st}$ image data for object recognition. The particle map calculating module 632 couples to the 3D image calculating module 631 to receive the 2D image and to the particle detector 620 to receive the $2^{nd}$ image data. The $2^{nd}$ image data may include the object morphology and can also show the distribution of the target particle. The 2D image from the image sensor 610 only contains object morphology. Therefore, the particle map calculating module 632 can obtain the particle map data which includes the particle distribution information according to a comparison between the 2D image and the $2^{nd}$ image data. The particle map data only carries information about the optical absorption of the target particles along the line of sight of each pixel. The natural logarithm of optical absorption of the target particles can translate to be the column density which is a product of path length and concentration. Therefore, the processor 630 can obtain the concentration result by obtaining the path length and performing mathematical calculations on the particle map data.

The concentration calculating module 633 couples to the 3D image calculating module 631 to receive the depth map data and to the particle map calculating module 632 to receive the particle map data. The depth map data from the image sensor 610 contains the path length information. Then, the concentration calculating module 633 can determine the concentration result according to the depth map data and the particle map data.

In an implementation, the image sensor 610 is configured to operate at a first wavelength $\lambda_A$, and the optical power of the light emitter 612 of the image sensor is $P_{out}(\lambda_A)$. The particle detector 620 is configured to operate at wavelength $\lambda_B$, and the optical power of the light emitter 622 of the particle detector 620 is $P_{out}(\lambda_B)$. The reflectance of the object (e.g., driver's face) for the wavelength $\lambda_A$ is $R_{\lambda_A}$, and the reflectance for the wavelength $\lambda_B$ is $R_{\lambda_B}$. The distance to the object of each i, j pixel is $d(x_i, y_j)$ which can be obtained from the depth map data. Here $x_i$ and $y_j$ are the physical 2D coordinates imaged into the given i, j pixel. Then, when the target particle is not present, the 2D image from the image sensor 610 is $P_{\lambda_A}(i, j)$ which is reflected from the object and received by each i, j pixel of the image sensor 610. $P_{\lambda_A}(i, j)$ is $$P_{\lambda_A}(i, j) \propto \frac{P_{out}(\lambda_A) \times R_{\lambda_A}(x_i, y_j)}{d(x_i, y_j)^2}$$

The $2^{nd}$ image data from the particle detector 620 is $P_{\lambda_B}(i, j)$ which is reflected from the object and received by each i, j pixel of the particle detector 620. $P_{\lambda_B}(i, j)$ is $$P_{\lambda_B}(i, j) \propto \frac{P_{out}(\lambda_B) \times R_{\lambda_B}(x_i, y_j)}{d(x_i, y_j)^2}$$

For simplicity, all angle-of-incidence and emission-profile related effects are lumped into the reflection $R_{\lambda_A}$ and $R_{\lambda_B}$. When the target particle is not present, the particle map data $P_0(i, j)$ generated by the particle map calculating module 632 can be derived by a ratio of the $2^{nd}$ image data $P_{\lambda_A}(i, j)$ to the 2D image $P_{\lambda_B}(i, j)$.

$$P_0(i, j) = \frac{P_{\lambda_B}(i, j)}{P_{\lambda_A}(i, j)} = \frac{P_{out}(\lambda_B) \times R_{\lambda_B}(x_i, y_j)}{P_{out}(\lambda_A) \times R_{\lambda_A}(x_i, y_j)}$$

In an implementation, the wavelength $\lambda_B$ can be 1310 nm, which is outside of the absorption band of ethanol. The wavelength $\lambda_A$ can be 1393 nm, which is within the absorption band of ethanol. The wavelengths $\lambda_A$ and $\lambda_B$ are close enough and have similar reflection coefficients $R_{\lambda_A}$ and $R_{\lambda_B}$ relative to the driver's face. Therefore, when the target particle is not present, $$R_{\lambda_A}(x_i, y_j) \cong R_{\lambda_B}(x_i, y_j)$$

$$P_0(i, j) = \frac{P_{\lambda_B}(i, j)}{P_{\lambda_A}(i, j)} = \frac{P_{out}(\lambda_B)}{P_{out}(\lambda_A)} = P_{BA}$$

The quantity $P_{BA}$ can be a system calibration parameter and can be obtained from the ratio of the image sensor's and particle detector's light output power $P_{out}$. In an implementation, the $P_{BA}$ can be obtained when the detection apparatus starts to operate and is stored in a memory or automatically calibrated periodically to reduce the drift caused by temperature and aging.

When the target particle is present, the particle map data P(i, j) can be derived by $$2D\text{ image} = P_{\lambda_A}(i, j) = \frac{P_{out}(\lambda_A) \times R_{\lambda_A}(x_i, y_j)}{d(x_i, y_j)^2}$$

$$2nd\text{ image data} = P_{\lambda_B}(i, j) = \frac{P_{out}(\lambda_B) \times R_{\lambda_B}(x_i, y_j)}{d(x_i, y_j)^2} \times e^{-2 \times n_{i,j} \times \sigma(\lambda_B) \times d(x_i, y_j)}$$

$$P(i, j) = \frac{P_{\lambda_B}(i, j)}{P_{\lambda_A}(i, j)} \cong \frac{P_{out}(\lambda_B)}{P_{out}(\lambda_A)} \times e^{-2 \times n_{i,j} \times \sigma(\lambda_B) \times d(x_i, y_j)} = P_{BA} \times e^{-2 \times n_{i,j} \times \sigma(\lambda_B) \times d(x_i, y_j)}$$

Here $n_{i,j}$ is the average concentration of the target particle (e.g., ethanol) in the air along the path length of each pixel, and $\sigma(\lambda_B)$ is the absorption of the target particle relative to wavelength $\lambda_B$. For example, ethanol vapor dispersed in the air, $\sigma(\lambda_B) \approx 0.9 \times 10^{-20}$ cm$^2$. Hence, the average concentration $n_{i,j}$ of each pixel can be derived by $$n_{i,j} = \frac{1}{2 \times \sigma(\lambda_B) \times d(x_i, y_j)} \times \ln \frac{P_{BA}}{P(i, j)}$$

Therefore, the concentration calculation module 633 can obtain the average concentration $n_{i,j}$ of each pixel through the particle map data P(i, j) and the depth map data $d(x_i, y_j)$. In one embodiment, the concentration calculation module 633 can output the average concentration as the concentration result. The concentration result can be determined by the concentration calculating module 633 by averaging $n_{i,j}$ of each pixel or selecting the maximum value of $n_{i,j}$. The average concentration may be lower than the peak concentration. The automatic ignition device can deactivate the ignition device when the average concentration of alcohol detected by an alcohol detection apparatus installed in the car exceeds a threshold.

In another embodiment, the concentration calculation module 633 can output the total amount of the target particle as the concentration result, such as the total amount of alcohol exhaled in the driver's single breath. $\Delta x_i \times \Delta y_j$ is the unit projection area corresponding to each i, j pixel on the object, and the distance from each i, j pixel to the unit projection area $\Delta x_i \times \Delta y_j$ is $d(x_i, y_j)$. Then, a volume element corresponding to each i, j pixel to the object can be represented by a physical pyramid $dV_{i,j}$.

$$dV_{i,j} = \frac{1}{3} \times d(x_i, y_j) \times \Delta x_i \times \Delta y_j$$

The following is the calculation formula for the total amount m of a target particle. The total amount m of target particle can be obtained by integrating the average concentration $n_{i,j}$ over all the pyramid volume element $dV_{i,j}$. $\mu$ is the molecular weight of the target particle, and the unit projected area $\Delta x_i \times \Delta y_j$ can be represented by $\Delta S_{i,j}$.

$$m = \mu \times \sum_{i,j} n_{i,j} \times dV_{i,j} = \frac{\mu}{6 \cdot \sigma(\lambda_B)} \times \sum_{i,j} \Delta S_{i,j} \times \ln \frac{P_{BA}}{P(i, j)}$$

The total amount of a target particle m can be regarded as the weighted sum of each pixel value in the particle map data P(i, j). The weighting coefficient is the corresponding unit projected area $\Delta S_{i,j}$. When the target particle is not present, $P(i, j) = P_{BA}$, the total amount of target particle m is calculated to be zero. In an implementation, when the target particle is alcohol, the ethanol molecular weight $\mu = 7.65 \times 10^{-26}$ kg.

The above summation equation of the total amount of target particle m also can be expressed in terms of $\Delta\theta_x$ and $\Delta\theta_y$ which are the per-pixel angular resolutions of the image sensor 610. It is assumed that $\Delta\theta_x$ and $\Delta\theta_y$ are both small. The calculation formula for the total amount of a target particle m is as follows:

$$dV_{i,j} = \frac{1}{3} \times d(x_i, y_j) \times \Delta x_i \times \Delta y_j = \frac{1}{3} \times d^3(x_i, y_j) \times \Delta\theta_x \times \Delta\theta_y$$

-continued $$m=\mu\times\sum_{i,j}n_{i,j}\times dV_{i,j}=\frac{\mu}{2\times\sigma(\lambda_B)}\times\sum_{i,j}\frac{dV_{i,j}}{d(x_i,y_j)}\times\ln\frac{P_{BA}}{p_{i,j}}=$$

$$\frac{\mu\times\Delta\theta_x\times\Delta\theta_y}{6\times\sigma(\lambda_B)}\times\sum_{i,j}d(x_i,y_j)^2\times\ln\frac{P_{BA}}{P(i,j)}$$

The total amount of a target particle m can be regarded as the weighted sum of each pixel value in the particle map data P(i, j). The weighting coefficient is related to the depth map data $d(x_i, y_i)$ obtained from the image sensor 610 operation.

Therefore, the detection apparatus 600 can obtain the object recognition through the 3D image and simultaneously (during at least a portion of overlapping time periods) obtain the presence or concentration of the target particle through the concentration result. The detection apparatus 600 may require about tens of milliseconds to obtain a few frames including the depth image to determine the 3D image and obtain particle concentration information at the same time.

In another implementation, the particle map calculating module 632 of the processor 630 can couple to the image sensor 610 and obtain 2D image from $1^{st}$ image data. The concentration calculation module 633 of the processor can couple to the image sensor 610 and obtain depth map data from $1^{st}$ image data.

Figure 7:
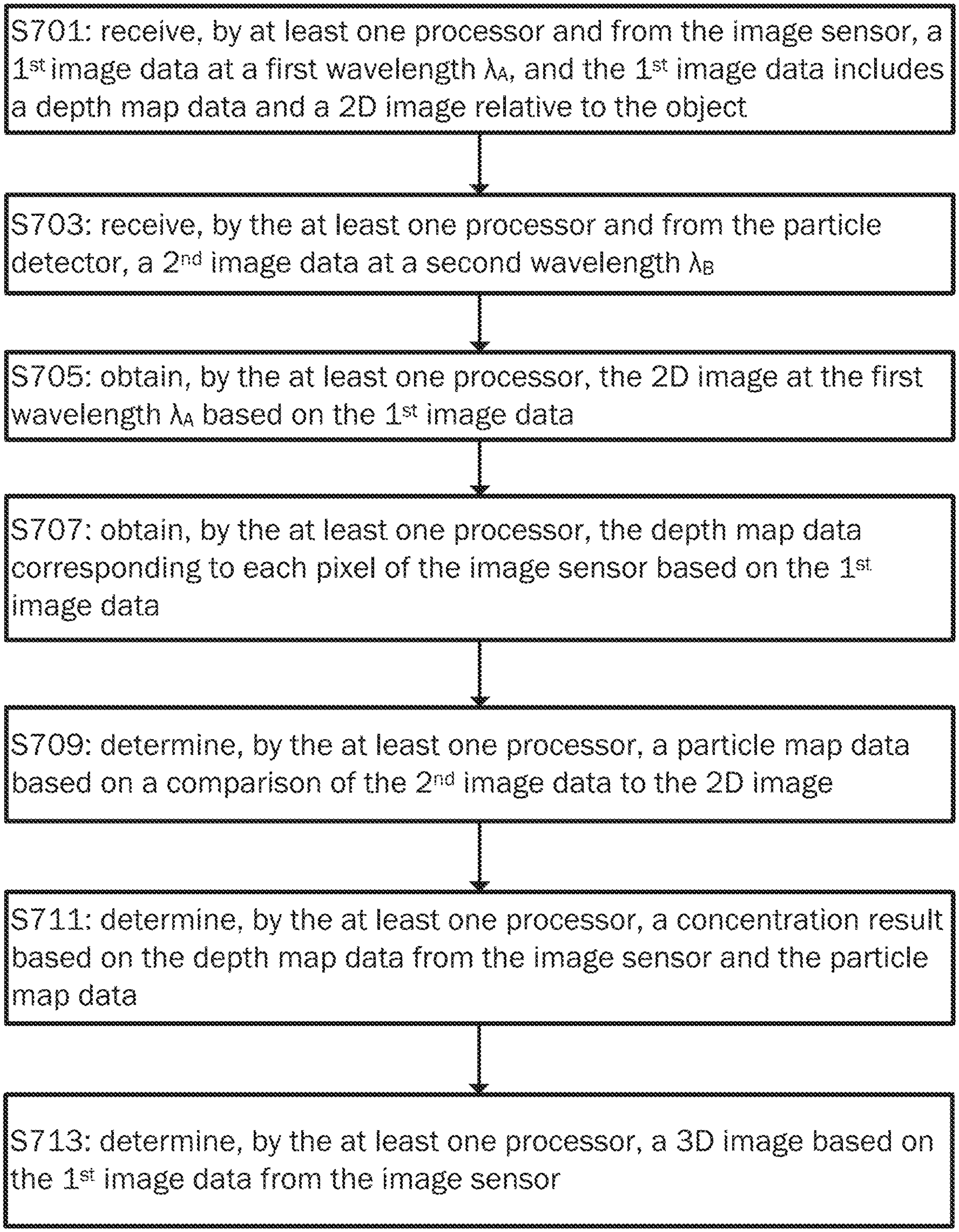
FIG. 7 shows a flowchart for detecting target particles of a detection apparatus in accordance with another embodiment of the present disclosure.

FIG. 7 shows a flow for detecting target particles of a detection apparatus in accordance with another embodiment of the present disclosure. In S701, at least one processor of the detection apparatus receives a $1^{st}$ image data at a first wavelength $\lambda_A$ from the image sensor. The $1^{st}$ image data includes the depth map data and the 2D image relative to the object. In S703, the at least one processor of the detection apparatus receives a $2^{nd}$ image data at a second wavelength $\lambda_B$ from the particle detector. In S705, the at least one processor of the detection apparatus obtains the 2D image at the first wavelength $\lambda_A$ based on the $1^{st}$ image data. In S707, the at least one processor of the detection apparatus obtains the depth map data corresponding to each pixel of the image sensor based on the $1^{st}$ image data. In S709, the at least one processor of the detection apparatus determines a particle map data based on a comparison of the $2^{nd}$ image data from the particle detector to the 2D image from the image sensor. The comparison method can use a calculation of difference, ratio, or other suitable mathematical calculation. In S711, the at least one processor of the detection apparatus determines a concentration result based on the depth map data from the image sensor and the particle map data. In S713, the at least one processor of the detection apparatus determines a 3D image based on the $1^{st}$ image data from the image sensor. The order of steps S701 to S707 may vary depending on the implementations. For example, the order of S701 and S703 can be exchanged, the order of S705 and S707 is exchanged, or the order of S703 and S705 can be exchanged.

Figure 8:
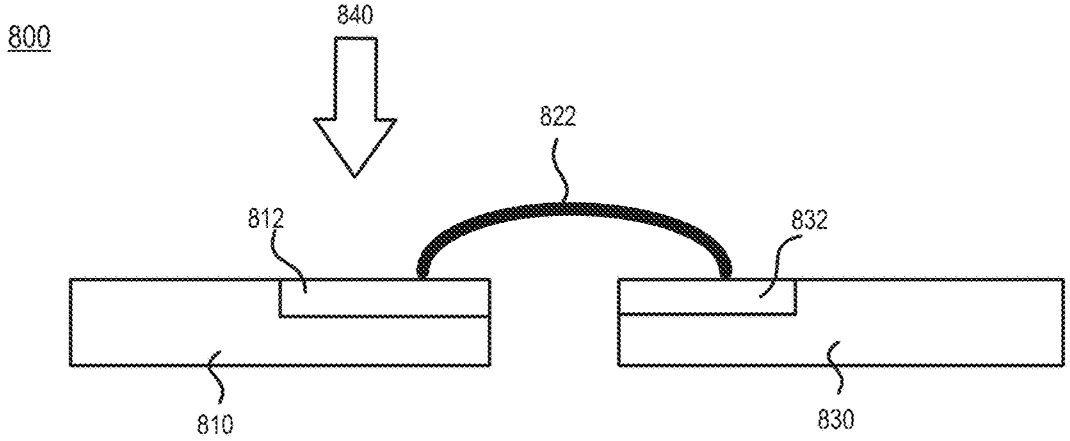
FIG. 8 shows an optical detector in accordance with one embodiment of the present disclosure.

FIG. 8 illustrates an optical detector 800, which can be an example of the optical detector 122. An optical detector 800 includes a first substrate 810 and a second substrate 830. The first substrate 810 includes a sensing area 812 (e.g., III-V material) that is electrically coupled to sensing circuitry 832 (e.g., CMOS circuitry) of the second substrate 830 via wire(s) 822 (e.g., wire-bonded).

Figure 9:
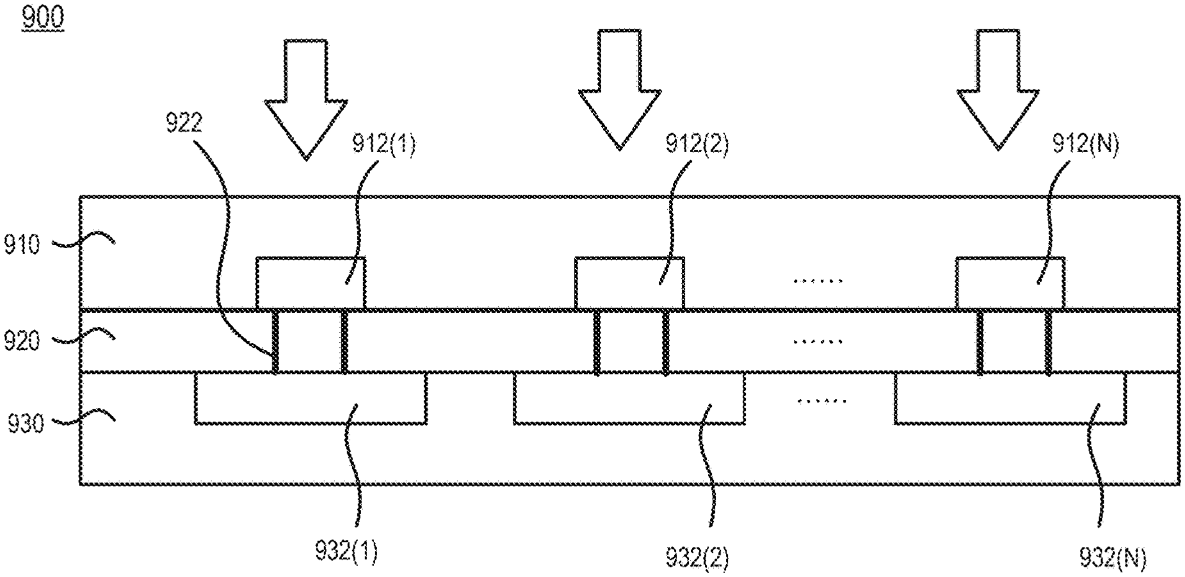
FIG. 9 shows an optical detector in accordance with another embodiment of the present disclosure.

FIG. 9 illustrates an optical detector 900, which can be another example of the optical detector 122. The optical detector 900 includes a first substrate 910 and a second substrate 930, which can both be silicon substrates. The first substrate 910 and the second substrate 930 are wafer-bonded via a bonding interface 920 (e.g., oxide or any other suitable materials). The first substrate 910 includes multiple sensing areas 912(1)~912(N), where N is a positive integer. In some implementations, the first substrate 910 is a silicon substrate and the multiple sensing areas 912(1)~912(N) may be comprised of germanium that is deposited on the first substrate 910. The second substrate 930 includes multiple corresponding circuitry areas 932(1)~932(N). The multiple sensing areas 912(1)~912(N) and the multiple corresponding circuitry areas 932(1)~932(N) are electrically coupled through the bonding interface 920 via wires 922.

Various means can be configured to perform the methods, operations, and processes described herein. For example, any of the systems and apparatuses (e.g., optical sensing devices and related circuitry) can include unit(s) and/or other means for performing their operations and functions described herein. In some implementations, one or more of the units may be implemented separately. In some implementations, one or more units may be a part of or included in one or more other units. These means can include processor(s), microprocessor(s), graphics processing unit(s), logic circuit(s), dedicated circuit(s), application-specific integrated circuit(s), programmable array logic, field-programmable gate array(s), controller(s), microcontroller(s), and/or other suitable hardware. The means can also, or alternately, include software control means implemented with a processor or logic circuitry, for example. The means can include or otherwise be able to access memory such as, for example, one or more non-transitory computer-readable storage media, such as random-access memory, read-only memory, electrically erasable programmable read-only memory, erasable programmable read-only memory, flash/other memory device(s), data register(s), database(s), and/or other suitable hardware.

As used herein, the terms such as "first", "second", "third", etc. describe various elements, components, regions, layers and/or sections, these elements, components, regions, layers and/or sections should not be limited by these terms. These terms may be only used to distinguish one element, component, region, layer, section, signal, or operation from another. The terms such as "first", "second", "third", etc. when used herein do not imply a sequence or order unless clearly indicated by the context. The terms "light-receiving", "light-detecting", "light-sensing" and any other similar terms can be used interchangeably.

Aspects of the disclosure have been described in terms of illustrative embodiments thereof. Numerous other embodiments, modifications, and/or variations within the scope and spirit of the appended claims can occur to persons of ordinary skill in the art from a review of this disclosure. Any and all features in the following claims can be combined and/or rearranged in any way possible. Accordingly, the scope of the present disclosure is by way of example rather than by way of limitation, and the subject disclosure does not preclude inclusion of such modifications, variations or additions to the present subject matter as would be readily apparent to one of ordinary skill in the art. Moreover, terms are described herein using lists of example elements joined by conjunctions such as "and," "or," "but," etc. It should be understood that such conjunctions are provided for explanatory purposes only. Lists joined by a particular conjunction such as "or," for example, can refer to "at least one of" or "any combination of" example elements listed therein. Also, terms such as "based on" should be understood as "based at least in part on".

Those of ordinary skill in the art, using the disclosures provided herein, will understand that the elements of any of the claims discussed herein can be adapted, rearranged, expanded, omitted, combined, or modified in various ways without deviating from the scope of the present disclosure.

While the disclosure has been described by way of example and in terms of a preferred embodiment, it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A method for detecting target particles in a detection apparatus, the method comprising:

receiving, by at least one processor of the detection apparatus, a first image data at a first wavelength from an image sensor of the detection apparatus;

receiving, by the at least one processor of the detection apparatus, a second image data at a second wavelength from a particle detector of the detection apparatus;

obtaining, by the at least one processor of the detection apparatus, a 2D image based on the first image data;

obtaining, by the at least one processor of the detection apparatus, depth map data based on the first image data;

obtaining, by the at least one processor of the detection apparatus, a particle map data based on a ratio of the second image data to the 2D image; and determining, by the at least one processor of the detection apparatus, a concentration result based on the depth map data and the particle map data.

2. The method of claim 1, further comprising determining, by the at least one processor of the detection apparatus, a 3D image based on the first image data.

3. The method of claim 1, further comprising storing, by the at least one processor of the detection apparatus, a calibration parameter obtained from a ratio of light output power of the image sensor and the particle detector.

4. The method of claim 3, wherein determining, by the at least one processor of the detection apparatus, the concentration result is further based on the calibration parameter.

5. The method of claim 1, wherein the image sensor comprises a plurality of photodetectors forming a pixel array and at least one light emitter.

6. The method of claim 5, wherein at least a portion of the pixel array is a time-of-flight sensor.

7. The method of claim 1, wherein the particle detector comprises a light emitter and an optical detector.

8. The method of claim 7, wherein the optical detector comprises germanium (Ge), tin (Sn), and silicon (Si).

9. The method of claim 1, wherein the first wavelength is different from the second wavelength.

10. The method of claim 1, wherein light with the first wavelength is not absorbed by the target particles.

11. The method of claim 1, wherein the at least one processor includes a 3D image calculating module configured to provide a 3D image, a particle map calculating module configured to provide the particle map data, and a concentration calculating module configured to provide the concentration result.

12. The method of claim 1, wherein the particle map data contains particle distribution information.

13. The method of claim 1, wherein the concentration result is an average concentration of the target particles.

14. The method of claim 1, wherein the concentration result is a total amount of the target particles.

15. A detection apparatus configured to detect target particles, comprising:

an image sensor configured to provide a first image data at a first wavelength;

a particle detector configured to provide a second image data at a second wavelength; and at least one processor coupled to the image sensor and the particle detector and configured to:

receive the first image data;

receive the second image data;

obtain a 2D image based on the first image data;

obtain depth map data based on the first image data;

obtain a particle map data based on a ratio of the second image data to the 2D image; and determine a concentration result based on the depth map data and the particle map data.

16. The detection apparatus of claim 15, wherein the at least one processor is configured to determine a 3D image based on the first image data.

17. The detection apparatus of claim 15, wherein the at least one processor is configured to store a calibration parameter obtained from a ratio of light output power of the image sensor and the particle detector.

18. The detection apparatus of claim 17, wherein the at least one processor is configured to determine the concentration result further based on the calibration parameter.

19. The detection apparatus of claim 15, wherein the image sensor comprises a plurality of photodetectors forming a pixel array and at least one light emitter.

20. The detection apparatus of claim 19, wherein at least a portion of the pixel array is a time-of-flight sensor.

* * * * *